(12) United States Patent
Garris et al.

(10) Patent No.: US 6,426,317 B1
(45) Date of Patent: Jul. 30, 2002

(54) STABLE, HIGH AVAILABLE HALOGEN 1,3,5-TRIAZINE-2,4,6-TRIONE COMPOSITIONS HAVING RAPID DISSOLUTION RATES

(75) Inventors: John P. Garris, Suwanee; Christopher Reed, Loganville; Michael Engram, Conyers, all of GA (US)

(73) Assignee: Great Lakes Chemical Corporation, West Lafayette, IN (US)

( * ) Notice: Subject to any disclaimer, the term of this patent is extended or adjusted under 35 U.S.C. 154(b) by 0 days.

(21) Appl. No.: 09/430,760

(22) Filed: Oct. 29, 1999

(51) Int. Cl.$^7$ .................. A01N 43/64; A01N 25/00; A01N 55/00; A01N 59/00
(52) U.S. Cl. .................. 504/227; 424/405; 424/489; 424/499; 424/501; 424/657; 424/658; 424/659; 424/660; 424/682; 514/769; 514/770; 514/771; 514/772.1; 514/772.3; 514/781; 514/949; 514/950; 514/241; 504/116.1; 504/118; 504/120; 504/121; 504/122; 504/123; 504/124; 504/126; 504/133; 504/150; 504/151; 504/152; 504/153; 504/155; 504/189; 504/190; 504/193; 504/358; 504/360; 504/367
(58) Field of Search .................. 424/465, 494, 424/657, 658, 659, 660, 682, 722, 724, 405, 489, 499, 501; 514/241, 769, 770, 772, 772.1, 772.2, 772.3, 772.4, 772.5, 772.6, 777.7, 777, 781, 949, 950, 960, 961, 970, 975; 504/116.1, 118, 120, 121, 122, 123, 124, 126, 133, 150, 151, 152, 153, 155, 189, 190, 193, 227, 358, 360, 367

(56) References Cited

U.S. PATENT DOCUMENTS

| | | | | |
|---|---|---|---|---|
| 3,367,876 A | * | 2/1968 | Keast et al. | 510/381 |
| 4,389,318 A | | 6/1983 | Wojtowicz | 210/755 |
| 4,472,187 A | | 9/1984 | Wojtowicz | 71/67 |
| 4,498,921 A | | 2/1985 | Wojtowicz | 71/67 |
| 4,594,091 A | | 6/1986 | Girvan | 71/67 |
| 5,021,186 A | | 6/1991 | Ota et al. | 252/186.35 |
| 5,131,938 A | | 7/1992 | Girvan | 71/67 |
| 5,164,109 A | | 11/1992 | Wojtowicz | 252/175 |
| 5,178,787 A | | 1/1993 | Hung et al. | 252/90 |
| 5,330,676 A | | 7/1994 | Glen | 252/186.35 |
| 5,338,461 A | | 8/1994 | Jones | 210/755 |
| 5,478,482 A | | 12/1995 | Jones et al. | 210/753 |
| 5,498,415 A | | 3/1996 | Jones | 424/409 |
| 5,510,108 A | | 4/1996 | Chouraqui | 424/408 |
| 5,514,287 A | | 5/1996 | Jones et al. | 210/753 |
| 5,541,150 A | | 7/1996 | Garris | 504/152 |
| 5,614,528 A | | 3/1997 | Jones et al. | 514/258 |
| 5,648,314 A | | 7/1997 | Lachocki et al. | 504/151 |
| 5,670,451 A | | 9/1997 | Jones et al. | 504/134 |
| 5,674,429 A | | 10/1997 | Lachocki et al. | 252/186.28 |
| 5,676,844 A | | 10/1997 | Girvan | 210/756 |

OTHER PUBLICATIONS

WEST online, file JPAB (Ota et al., JP 02129102 A (1990)), Abstract.*
STN/CAS online, file CAPLUS, Acc. No. 1980:175770, Doc. No. 92:175770, (Nakagi et al., JP 54160730 (1979)), Abstract.*
STN/CAS online, file CAPLUS, Acc. No. 1989:19848, Doc. No. 110:19848, (Kamiyama et al., JP 63088108 (1988)), Abstract.*
STN/CAS online, file CAPLUS, Acc. No. 1982:77894, Doc. No. 98:77894, (JP 57171981 (1982)), Abstract.*

* cited by examiner

*Primary Examiner*—Jose' G. Dees
*Assistant Examiner*—Frank Choi
(74) *Attorney, Agent, or Firm*—Woodard, Emhardt, Naughton Moriarty & McNett

(57) ABSTRACT

Dry, stable, high available halogen sanitizing granular compositions with a rapid rate of dissolution comprising halogenated 1,3,5-triazine-2,4,6-triones and a dissolution accelerant that is an alkali metal salt of 1,3,5-triazine-2,4,6-trione are disclosed. The disclosed compositions may include inorganic and/or organic disintegration agents. Additionally, these compositions may contain other performance enhancing additives such as water clarifiers, algaestats/algaecides, surfactants, glidants, processing aids, and binders. These UV stable sanitizing compositions contain a high available halogen content, and are stable even when stored in high-humidity environments.

22 Claims, 1 Drawing Sheet

STABLE, HIGH AVAILABLE HALOGEN 1,3,5-TRIAZINE-2,4,6-TRIONE COMPOSITIONS HAVING RAPID DISSOLUTION RATES

FIELD OF THE INVENTION

The present invention relates generally to sanitizing compositions for controlling microbial growth in recirculating water systems, and more particularly to stable, high available halogen 1,3,5-triazine-2,4,6-trione compositions with a rapid dissolution rate.

BACKGROUND OF THE INVENTION

Halogen compounds, particularly those with chlorine and bromine, have long been used as sanitizers to kill bacteria, fungi, and algae in recirculating water systems. These halogen sanitizing compounds are relatively low in cost and provide broad-spectrum control even at low (ppm) concentrations.

Sodium hypochlorite, lithium hypochlorite and calcium hypochlorite are among the most popular halogen sanitizing compounds, in part because they have high dissolution rates or disperse readily in water. This characteristic is beneficial when it is necessary to provide high halogen levels to recirculating water systems in a short period of time (often referred to as slug-feeding, shocking, or superchlorination).

Of the inorganic halogen sanitizing compounds, calcium hypochlorite, which contains 65% to 75% available halogen, is the most widely used dry granular material because of its low cost and high halogen content. Sodium hypochlorite and lithium hypochlorite, while capable sanitizing compounds, are less cost-effective and have lower available halogen relative to calcium hypochlorite.

A significant weakness of all the above inorganic compounds is their susceptibility to ultraviolet (UV) light degradation when used in an outdoor recirculating water system. As is known to the art, UV light reduces halogen levels in water, thus reducing the inorganic compounds' ability to disinfect and sanitize. To address that weakness, the prior art has used inorganic compounds in combination with separate UV stabilizers, the best known of which is 1,3,5-triazine-2,4,6-trione (cyanuric acid), to address this weakness.

A more specific problem is associated with calcium hypochlorite. The National Fire Protection Association (NFPA) categorizes calcium hypochlorite as a Class 3 oxidizer. The NFPA code defines a Class 3 oxidizer as "an oxidizer that will cause a severe increase in the burning rate of combustible materials with which it comes in contact or that will undergo vigorous self-sustained decomposition due to contamination or exposure to heat," NFPA 430: Code for the Storage of Liquid and Solid Oxidizers, 1995 edition, p. 430–5.

One alternative to inorganic halogen sanitizing compounds is the class of halogenated 1,3,5-triazine-2,4,6-triones. The acid forms of halogenated 1,3,5-triazine-2,4,6-triones such as 1,3,5-trichloro-1,3,5-triazine-2,4,6-trione (trichloroisocyanuric acid) and dichloro-1,3,5-triazine-2,4,6-trione (dichloroisocyanuric acid) have high available halogen, 90% and 70% respectively. The high available halogen content and the intrinsic UV stabilizer (cyanuric acid) contained in these materials provides a cost effective, widely used sanitizing compound to treat outdoor recirculating water systems. The NFPA categorizes halogenated 1,3,5-triazine-2,4,6-triones as Class 1 oxidizers. NFPA defines Class 1 oxidizers as "an oxidizer whose primary hazard is that it slightly increases the burning rate but does not cause spontaneous ignition when it comes in contact with combustible materials," NFPA 430: Code for the Storage of Liquid and Solid Oxidizers, 1995 edition, p. 430–5.

However, the halogenated 1,3,5-triazine-2,4,6-triones have slow dissolution rates as a result of low solubility. This makes the halogenated 1,3,5-triazine-2,4,6-triones less desirable when rapid halogen delivery is desired. In view of this limitation, compositions like trichloroisocyanuric acid have been compressed into tablets and used in conditions where a slow or sustained release is desired. For instance, continuous or semi-continuous erosion feeding of these compositions has been effective in delivering a sanitizing amount of hypochlorous acid over a period of days as reported in U.S. Pat. No. 5,648,314 to Lachocki et al., U.S. Pat. No. 5,514,287 to Jones et al., U.S. Pat. No. 5,510,108 to Chouraqui, and U.S. Pat. No. 5,498,415 to Jones.

Other organic alternatives to the halogenated 1,3,5-triazine-2,4,6-triones for applications when rapid halogen delivery is desired are the anhydrous alkali metals salts of the acids (e.g., sodium or potassium dichloroisocyanurate). The sodium and potassium dichloroisocyanurate salts are effective sanitizers, but have reduced available halogen contents (62% and 58% respectively). Furthermore, these salts are categorized by the NFPA as Class 3 oxidizers. Sodium dichloroisocyanurate can be hydrated, reducing the NFPA oxidizer categorization to a Class 1 oxidizer, but hydrating sodium dichloroisocyanurate further reduces the available halogen content—making the sanitizing compound less cost effective.

The following table compares the important characteristics of the previously described halogen sanitizing compounds.

| Sanitizer | Available Halogen | Oxidizer Rating[1] | Solubility[2] | Contains UV Stabilizer |
|---|---|---|---|---|
| Calcium hypochlorite | 65–75% | 3 | ≅22[3] | No |
| Sodium hypochlorite (liquid) | 5–15% | N/A | N/A | No |
| Lithium hypochlorite | 35% | 2 | ≅43[3] | No |
| Sodium dichloro-isocyanurate anhydrous | 60–63% | 3 | 12.5[4] | Yes |
| Sodium dichloro-isocyanurate dihydrate | 56% | 1 | 12.5[4] | Yes |
| Potassium dichloro-isocyanurate anhydrous | 58% | 3 | 5.0[4] | Yes |
| Trichloroisocyanuric acid | 85–91% | 1 | 1.2[4] | Yes |
| Dichloroisocyanuric acid | 70% | 1 | 0.7[4] | Yes |

[1]Oxidizers are categorized on a scale from 1 to 4 based on National Fire Protection Association (NFPA) codes. NFPA 430: Code for the Storage of Liquid and Solid Oxidizers, 1995 edition.
[2]Solubility in water at 20° C. reported as g/100g (%)
[3]The Proper Management of Pool and Spa Water, Hydrotech Chemical Corporation, 1988
[4]Swimming Pool Disinfection with Chlorinated-s-Triazine Trione Products, Special Report 6862, Monsanto Company, May 1975.

Several attempts have been made to develop a commercially viable, rapidly dissolving, high available halogen 1,3,5-triazine-2,4,6-trione sanitizing composition. For example, Wojtowicz discloses rapid dissolving mixtures containing trichloroisocyanuric acid and alkali metal bicarbonates in U.S. Pat. No. 4,389,318. Wojtowicz also discloses rapid dissolving mixtures containing trichloroisocyanuric acid and alkaline earth metal salts of carbonate, hydroxide, oxide, and mixtures thereof in U.S. Pat. Nos. 4,472,187 and 4,498,921. In U.S. Pat. No. 4,599,411, Wojtowicz discloses a mixture of trichloroisocyanuric acid, cyanuric acid, and sodium bicarbonate. However, the Wojtowicz mixtures were never commercialized.

Therefore, a need exists for stable, high dissolution rate halogenated 1,3,5-triazine-2,4,6-trione sanitizing compositions with high available halogen content. A need also exists for rapid halogen delivery sanitizing compositions that have a substantially greater half-life in the presence of UV light than inorganic halogen compositions. A need further exists for sanitizing compositions that have high amounts of available halogen in combination with other additives that provide additional benefits to recirculating water systems. The present invention addresses all of these needs.

SUMMARY OF THE INVENTION

Briefly describing one aspect of the present invention, there is provided a dry, stable, high available halogen sanitizing composition with a rapid rate of dissolution, comprising co-compacted granules of halogenated 1,3,5-triazine-2,4,6-trione and a dissolution accelerant that is an alkali metal salt of 1,3,5-triazine-2,4,6-trione.

In a further aspect of the present invention, the dissolution accelerant is replaced or supplemented by inorganic or organic disintegration agents.

In another aspect of the invention the dry, stable, high available halogen sanitizing composition further comprises additional water enhancing chemicals including: water clarifiers, flocculants, coagulants, algaestat/algaecides, and/or fungicides.

In a still further aspect of the invention, other ingredients such as dyes, surfactants, glidants, etc. may be included.

One object of the present invention is to provide a rapidly dissolving sanitizing composition of a high-available-halogen, low-solubility sanitizer, with the formulation being stable during manufacture and long-term storage.

A further object of the present invention is to provide a rapidly dissolving UV-stable sanitizing composition with a high available halogen content.

A further object of the present invention is to provide a method of applying the composition of the present invention to recirculating water.

Further aspects and advantages of the present invention will be apparent from the following description.

DESCRIPTION OF THE PREFERRED EMBODIMENT

Figure 1:
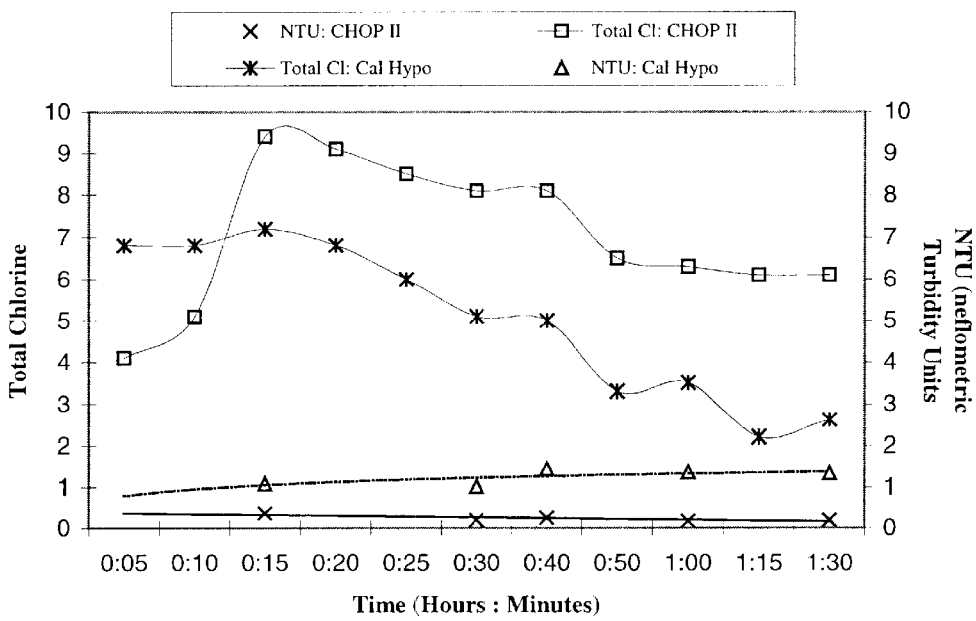
FIG. 1 is a graph of total chlorine and neflometric turbidity over time, comparing the present invention with calcium hypochlorite.

For the purpose of providing a further understanding of the principles of the invention, reference will now be made to the preferred embodiments of the present invention, and specific language will be used to describe the same. It will nevertheless be understood that no limitation of the scope of the invention is thereby intended, such alterations and further modifications in the illustrated invention, and such further applications of the principles of the invention as illustrated therein being contemplated as would normally occur to one skilled in the art to which the invention relates.

The present invention provides rapidly-dissolving, sanitizing compositions comprising a halogenated 1,3,5-triazine-2,4,6-trione, and an alkali metal salt 1,3,5-triazine-2,4,6-trione. An inorganic and/or organic disintegration agent may also be included to supplement or replace the alkali metal salt. Finally, other additives that provide additional benefits to recirculating water systems including water clarifiers, flocculants, coagulants, algaestat/algaecides (and/or fungicides), dyes, surfactants, glidants, etc. may be included.

The inventive compositions are surprisingly stable, even when contaminated by water. Accordingly, they are useful for providing sanitizing, clarifying, and algaestatic/algaecidal components to recirculating water systems like swimming pools, spas, hot tubs, toilet bowls, reflecting pools, industrial water systems, fountains, etc. The relative proportions of the various components, as well as potential substitutions therefore, are described below. Representative examples of the preparation and use of the compositions are also presented.

As previously indicated, 1,3,5-trichloro-1,3,5-triazine-2,4,6-trione (trichloroisocyanuric acid) is the preferred sanitizer used in the present invention, but it may be replaced by other high available halogen (e.g., greater than 65% available halogen), low-solubility oxidizers such as other halogenated 1,3,5-triazine-2,4,6-triones. In the preferred embodiments, the sanitizer has an available halogen content of at least about 70% (most preferably more than 85%), and a solubility in water at 20° C. of less than about 2% w/v.

The concentration of trichloroisocyanuric acid or its substitute in the compositions of the present invention is between about 40% to about 99% by weight. Preferably trichloroisocyanuric acid is present in an amount between about 50% to about 90%, and most preferably between about 60% to about 80% of the total weight of the composition. Consequently, in the most preferred embodiment, the compositions contain between about 54% to about 72% available halogen.

In the preferred embodiment of the invention, a dissolution aid such as an alkali metal salt of 1,3,5-triazine-2,4,6-triones is used. In producing the salt, the alkali metal reacts with 1,3,5-triazine-2,4,6-trione to form the mono-, di-, or ti-alkali metal salts. Sodium or potassium is the preferred alkali metal that may be donated by sodium hydroxide, sodium carbonate, sodium bicarbonate, and the like or the potassium analogs of the same. Sodium hydroxide is the most preferred donor. In the most preferred embodiment, the disodium salt of 1,3,5-triazine-2,4,6-trione (disodium cyanurate) is used.

The dissolution aid is added to the composition between about 1% to about 60%. The preferred embodiment of the invention adds between about 5% and about 40% with about 8% and about 20% being most preferred.

Highly alkaline components mixed with trichloroisocyanuric acid are well known in the art to decompose trichloroisocyanuric acid within said mixture. It was surprising, however, to find that the highly alkaline salts (e.g., disodium cyanurate) did not react to decompose the trichloroisocyanuric acid in either dry or humid environments. These environmental conditions may be present during the manufacture or storage of the product.

In an alternative embodiment of the invention, the disodium cyanurate may be supplemented or replaced by one or more disintegration agents that differ in composition from 1,3,5-triazine-2,4,6-trione. Various inorganic and organic disintegration agents may be used alone or in combination to increase the dissolution rate of trichloroisocyanuric acid. Useful inorganic agents include montmorilinite (e.g.

smectite, hectorite, and bentonite), laponite, and other clays that swell when exposed to water. Of these, natural or synthetic montmorillinite or laponite clays are most preferred. Amorphous silica may also be used as a disintegration agent and as a glidant. These compounds can be applied between about 0.1% to about 20%, with between about 1% to about 10% being preferred.

Organic disintegration agents may also be used. Organic disintegration agents include methyl cellulose, carboxymethyl cellulose, high molecular weight polyacrylate and/or polyacrylamide polymers, and polyvinyl pyrolidone or the cross-linked forms of the same. These compounds may be applied to the composition between about 0.1% to about 20% with about 1.0% to about 10% being preferred.

Water clarifying agents known to the art (also known as coagulating agents and flocculants) may also be added. Preferred water clarifying agents are aluminum containing complexes selected from the group aluminum sulfate, aluminum chlorohydrate, sodium aluminum sulfate complex, potassium aluminum sulfate complex, and the like. Hydrated aluminum sulfate is preferred. Aluminum sulfate having from about 2 to about 20 equivalents of water per mole of aluminum is more preferred. In alternative embodiments, the aluminum sulfate containing complex is a hydrated potassium aluminum sulfate complex, hydrated sodium aluminum sulfate complex, or the like. The water clarifying agent concentration may contain between about 1% to about 40%. Preferably the water clarifying agent is present between about 2% to about 30%. In the most preferred embodiment, water clarifying agent is present between about 4% to about 18%.

The rapid dissolution rate sanitizing composition also preferably includes an algaestat/algaecide (and/or fungicide) additive such as boron containing compounds. Preferred boron-containing compounds are selected from the group consisting of: boric acid, boric oxide (anhydrous boric acid), compounds having the formula $M_nB_xO_y \cdot ZH_2O$ (in which M is any alkali metal or alkaline earth cation, including, but not limited to, sodium, potassium, calcium and magnesium; n is equal to 1, 2 or 3; x is any whole number from 2 to 10; Y is equal to $3X/2+1$; and Z is equal to 0 to 18). The $M_nB_xO_y \cdot ZH_2O$ boron-containing compounds include: disodium tetraborate, disodium octaborate, sodium pentaborate, sodium metaborate, dipotassium tetraborate, potassium pentaborate, and hydrates thereof. The rapid dissolution rate sanitizing composition contains the boron compounds in amounts between about 1% to about 40%, more preferably about 2% to about 30%. In the most preferred embodiment, sodium tetraborate pentahydrate is present between about 4% to about 18%.

The sanitizing compositions of the present invention are preferably solid granulated products of any size or shape above 200 microns in diameter. Granulated trichloroisocyanuric acid sanitizing compositions are preferred over powdered trichloroisocyanuric acid sanitizing compositions because of inhalation hazards inherent to powders (respirable powders are particles or particle agglomerates less than about 10 microns in diameter). The preferred embodiment reduces this risk by processing powdered components into larger, non-respirable granules. A powder form of the sanitizing composition of the invention may be manufactured and may dissolve at a more rapid rate than granules due to the powder's higher surface area to volume ratio; however, increased handling hazards for application are not desirable in the present invention. The granules of the sanitizing compositions of the present invention are prepared by dry particle-size enlargement methods, preferably co-compaction or granulation.

For the purposes of this invention, co-compaction is understood to be the process whereby two or more powdered components are mixed together, compressed, and comminuted to provide co-compacted granules.

Additional components such as binders, tabletting aids, mold release agents, corrosion inhibitors, scale inhibitors, surfactants, glidants, or dyes may be incorporated into compositions of the present invention or the final granulated product. The selection of such components is within the capability of those skilled in the art.

In preparing the sanitizing composition of the present invention, the powder form of all the components are admixed using appropriate equipment selected by those skilled in the art of solid material processing. The admixed material is then processed into granules using appropriate equipment known to those skilled in the art of dry particle size enlargement.

Compositions of the present invention are preferably used to treat recirculating water systems like swimming pools, spas, hot tubs, toilet bowls, reflecting pools, industrial water systems, fountains, etc. The present invention will sanitize, clarify, and reduce algae in water systems by contacting a sanitizingly effective amount of the sanitizing composition of the present invention with the water system through an appropriate application method. Appropriate amounts and application methods can be determined by persons skilled in the art without undue experimentation. Such application methods may be manual or automatic.

Reference will now be made to specific examples. It is to be understood that the examples are provided to more completely describe preferred embodiments, and no limitation to the scope of the invention is intended thereby.

EXAMPLE 1

The procedure for Example 1 is generally as follows. This procedure is used to formulate components into halogen containing materials such as trichloroisocyanuric acid on a small scale. The test helps identify materials that increase or decrease the stability of a formulated composition containing a stable halogen material. Specifically, the addition of various components to the halogen containing material can result in significant changes to the halogen off-gassing profile of the formulated composition. A sodium thiosulfate titration is used to determine the off-gassing profile of the formulated composition. The volume of thiosulfate titrant is proportional to the amount of gaseous oxidant (chlorine, chloramine, etc.) released from the formula composition sample during the test. Higher titrant volumes indicate higher gassing—a result indicative of lower stability in the formulated composition. Conversely, lower titrant volumes are indicative of higher stability in the formulated composition. The test results are used to guide decisions relative to formulation component addition.

Blended powder samples were prepared for each formula composition. A two-gram sample of each test formula composition was placed in a 0.75-inch diameter dye-punch set and compressed with 400 lbs. of force for 15 minutes.

After the fifteen-minute cycle, the small wafer produced was transferred to a dry eight ounce sample container. In Example 1, a small beaker containing 5 ml of 15% potassium iodide (KI) was placed beside the wafer in the container, and the container was vapor sealed. The container (with the sample and the KI beaker) was carefully placed in an approximately 50° C. oven for 24 hours. After the sample set was removed from the oven and cooled, a one-ml aliquot from each sample was placed in 50 ml of deionized water and titrated with 0.100 N sodium thiosulfate. The volume of thiosulfate reagent used to titrate the available halogen in the KI solution was recorded.

The Example 1 results (Table 1) demonstrate high levels of aluminum sulfate, used as a water clarifier, and boric acid, used as a dry processing lubricant, do not significantly affect the off-gassing profile of trichloroisocyanuric acid. This is further documented in U.S. Pat. No. 5,674,429. The results also show the sodium tetraborate pentahydrate, used as an algaestat, sodium bicarbonate and sodium carbonate, both used as dissolution aids, increase gassing significantly.

TABLE 1

Off-gassing of various compressed powder trichloroisocyanuric acid formulas.

| Formulation | Titrant Volume (ml) |
| --- | --- |
| 100% trichloroisocyanuric acid | 2.65 |
| 74.5% trichloroisocyanuric acid and 25.5% aluminum sulfate | 3.05 |
| 74.5% trichloroisocyanuric acid and 25.5% boric acid | 1.10 |
| 74.5% trichloroisocyanuric acid and 25.5% sodium tetraborate pentahydrate | 12.75 |
| 74.5% trichloroisocyanuric acid and 25.5% sodium bicarbonate | 15.05 |
| 74.5% trichloroisocyanuric acid and 25.5% sodium carbonate | 7.5 |

EXAMPLE 2

Example 2 used the procedure described above for Example 1, except the KI beaker contained 10 ml of 30% KI. For Example 2, each formula composition contained fixed amounts of aluminum sulfate (8%) and boric acid (1%). The levels of these two components were fixed as a result of data obtained from Example 1.

The Example 2 results (Table 2) show sodium tetraborate pentahydrate has a reduced tendency to cause off-gassing in the presence of aluminum sulfate as stated in U.S. Pat. No. 5,674,429. The results also show that both sodium bicarbonate and sodium carbonate substantially increase the off-gassing of trichloroisocyanuric acid formula compositions. Because of this high relative off-gassing, a sign of instability, no further processing was attempted with these two additives.

TABLE 2

Off-gassing of various compressed powder trichloroisocyanuric acid formulas containing 8% aluminum sulfate and 1% boric acid.

| Formulation | Titrant Volume (ml) |
| --- | --- |
| 91.5% trichloroisocyanuric acid | 1.05 |
| 74.5% trichloroisocyanuric acid and 16.5% sodium tetraborate pentahydrate | 3.10 |
| 74.5% trichloroisocyanuric acid and 16.5% sodium bicarbonate | 8.95 |
| 74.5% trichloroisocyanuric acid and 16.5% sodium carbonate | 8.95 |

EXAMPLE 3

Example 3 was devised to approximate the co-compaction process. Co-compaction is a typical method used for dry particle size enlargement. The formula compositions produced in this example were tested for their stability and in some cases for their solubility. The components used included a dissolution aid: disodium cyanurate, and a disintegration agent: microcrystalline cellulose, Lattice® NT (FMC).

Again, blended powder samples were prepared for each formula composition. A 20-gram sample of each test formula composition was placed in a 2.0 inch diameter dyepunch set and compressed under 22 tons of force for 60 minutes using a Carver press. The compressed wafer was reduced to granules using a spatula and a mortar and pestle set. Properly sized granules were collected using a standard sieve shaker.

Approximately one gram of each granular formula composition sample was placed in an eight-ounce sample container. A beaker with 5 ml of 30% KI solution was placed in each sample container. The containers were vapor sealed and carefully placed in an approximately 50° C. oven for 24 hours. After the sample set was removed from the oven and cooled, a one-ml aliquot from each sample was placed in 50 ml of deionized water and titrated with 0.100 N sodium thiosulfate. The volume of thiosulfate reagent used to titrate the available halogen in the KI solution was recorded. Results are shown in Table 3.

The Example 3 results (Table 3) show the formula compositions containing constant levels of trichloroisocyanuric acid, aluminum sulfate, and boric acid with varying levels of disodium cyanurate, used as a dissolution aid, sodium tetraborate pentahydrate, used as an algaestat/algaecide, do not significantly affect the off-gassing profile of trichloroisocyanuric acid formula compositions. The microcrystalline cellulose, used as a disintegration agent moderately impacts the off-gassing of trichloroisocyanuric acid.

TABLE 3

Off-gassing of various granular trichloroisocyanuric acid formulas containing 8% aluminum sulfate and 1% boric acid.

| Formulation | Titrant Volume (ml) |
| --- | --- |
| 91% trichloroisocyanuric acid | 0.35 |
| 82.75% trichloroisocyanuric acid and 8.25% disodium cyanurate | 0.40 |
| 74.5% trichloroisocyanuric acid and 16.5% sodium tetraborate pentahydrate | 0.30 |
| 74.5% trichloroisocyanuric acid and 16.5% disodium cyanurate | 1.40 |
| 74.5% trichloroisocyanuric acid and 16.5% Lattice ® NT | 4.40 |
| 74.5% trichloroisocyanuric acid and 8.25% disodium cyanurate, and 8.25% sodium tetraborate pentahydrate | 0.60 |

Some of the relatively stable formulas reported in Table 3 were also tested for solubility using the following method. A one-gram granule sample of the formula composition to be tested was placed in a 200 ml solution of balanced swimming pool water. The balanced swimming pool water contained approximately 200 ppm calcium hardness and 125 ppm total alkalinity (pH≈7.5). A table stirring device that did not have a physical stirring apparatus (i.e. stir bar or paddle) gently agitated the samples for 15 minutes. This gentle agitation allowed a more realistic dissolution simulation with material being dissolved by water movement rather than the physical grinding caused by stirrers and paddles.

After the 15-minute dissolution period, the sample solution was filtered to remove any remaining undissolved granules. A one-ml aliquot of the filtered sample solution was placed in 25 ml of deionized water. The available halogen contained in the sample solution aliquot was titrated with 0.010 N sodium thiosulfate. All measurements were made in milliliters (ml) of titrant. A large titrant volume is indicative of a highly soluble formula. An approximate titrant volume of 9.6 ml 0.010N sodium thiosulfate would indicate all available halogen was fully dissolved in a 72.2% trichloroisocyanuric acid (approximately 65% available halogen) formula composition. Calcium hypochlorite with 65% available halogen and a relatively rapid dissolution rate was used as a control.

The Example 3 solubility data (Table 4) shows the 8.25% disodium cyanurate formula composition dissolves twice as fast as 100% trichloroisocyanuric acid. Additionally, the dissolution rate of the formula composition containing 16.5% disodium cyanurate is four times faster than the 100% trichloroisocyanuric acid dissolution rate. The dissolution rate of the formula composition containing 16.5% microcrystalline cellulose is twice the 100% trichloroisocyanuric acid dissolution rate. The formula composition containing 8.25% disodium cyanurate and 8.25% of sodium tetraborate pentahydrate exhibited an enhanced dissolution rate relative to 100% trichloroisocyanuric acid.

TABLE 4

Solubility of various granular trichloroisocyanuric acid formulas containing 8% aluminum sulfate and 1% boric acid versus 100% trichloroisocyanuric acid and calcium hypochlorite.

| Formulation | Titrant Volume (ml) |
| --- | --- |
| Calcium Hypochlorite (65% available chlorine) | 9.60 |
| 100% trichloroisocyanuric acid | 0.8 |
| 82.75% trichloroisocyanuric acid and 8.25%, disodium cyanurate | 1.70 |
| 74.5% trichloroisocyanuric acid and 16.5% disodium cyanurate | 3.20 |
| 74.5% trichloroisocyanuric acid and 16.5% Lattice ® NT | 1.70 |
| 74.5% trichloroisocyanuric acid and 8.25% disodium cyanurate, and 8.25% sodium tetraborate pentahydrate | 2.00 |

EXAMPLE 4

Generally, the procedure for Examples 4–6 is as follows. Approximately 4 to 6 pounds of blended powder sample formulations were prepared. The samples were processed into granules using a pilot scale roll compactor, mill, and sieve shaker.

For Example 4, a formula composition containing 74.5% trichloroisocyanuric acid, 8% aluminum sulfate, 9% sodium tetraborate pentahydrate, 5% disodium cyanurate, and 0.5% Cab-O-Sil® (Cabot) was formulated. Various disintegration agents and a surfactant were added to this formula composition.

Example 4 stability testing was performed by adding one gram of appropriately sized granules to an eight-ounce sample jar. A beaker of 5 ml 30% KI solution was placed in each sample container. Additionally, 100 µl of distilled water was added to contaminate the trichloroisocyanuric acid formulated compositions. Moisture contamination is used to "stress" the system relative to stability. Each sample jar was vapor sealed and the sample containers were carefully placed in an approximately 50° C. oven for 24 hours. After the sample set was removed from the oven and cooled, a one-ml aliquot from each sample was placed in 50 ml of deionized water and titrated with 0.100 N sodium thiosulfate.

The Example 4 stability data (Table 5) shows that relatively stable formulas containing a dissolution aid, disintegration agents, and/or a surfactant can be co-compacted into granules. The organic dissolution aid polyvinylpyrrolidone (Sigma) was the least stable in this group of samples. The inorganic clays GelWhite L (Southern Clay Products) and Van-Gel® O (Vanderbilt) were relatively stable. The surfactant Hostapur SAS 93G (Clariant) was also relatively stable in the formula composition.

TABLE 5

Off-gassing of various granular trichloroisocyanuric acid formulas containing 8% aluminum sulfate, 9% sodium tetraborate pentahydrate, 5% disodium cyanurate and 0.5% Cab-O-Sil ®

| Formulation | Titrant Volume (ml) |
| --- | --- |
| 74.5% trichloroisocyanuric acid and 3% Gel White L | 2.20 |
| 74.5% trichloroisocyanuric acid and 3% Van-Gel ® O | 2.80 |
| 74.5% trichloroisocyanuric acid and 3% Polyvinylpyrrolidone | 4.40 |
| 74.5% trichloroisocyanuric acid and 3% Hostapur SAS 93G | 2.10 |

Example 4 solubility testing was performed in the same manner as in Example 3. In Example 4, the Van-Gel® O formula composition had the highest dissolution rate relative to all other additives tested. Additionally, Gel White L, polyvinylpyrrolidone, and HostaPur SAS 93G significantly enhanced the dissolution rate. The results are recorded in Table 6.

TABLE 6

Solubility of various granular trichloroisocyanuric acid formulas containing 8% aluminum sulfate, 9% sodium tetraborate pentahydrate, 5% disodium cyanurate and 0.5% Cab-O-Sil ®

| Formulation | Titrant Volume (ml) |
| --- | --- |
| 74.5% trichloroisocyanuric acid and 3% Gel White L | 3.30 |
| 74.5% trichloroisocyanuric acid and 3% Van-Gel ® O | 4.90 |
| 74.5% trichloroisocyanuric acid and 3% Polyvinylpyrrolidone | 3.25 |
| 74.5% trichloroisocyanuric acid and 3% Hostapur SAS 93G | 3.05 |

EXAMPLE 5

A formula composition containing 72.5% trichloroisocyanuric acid, 8% aluminum sulfate, and 8% sodium tetraborate pentahydrate was prepared. Again, various disintegration agents were added to the formula composition. Additionally, a glidant was added. The formula compositions were processed as described above.

The Example 5 stability results (Table 7) show that the formula composition containing 11.5% disodium cyanurate had the highest relative stability of all the formula compositions evaluated. Two formula compositions, one containing 4.0% Hectabrite AW (American Colloid Co.), 3.0% Vee-Gum® T (Vanderbilt) and 4.5% disodium cyanurate and the other containing 3.0% Vee-Gum® T and 8.5% disodium cyanurate were relatively stable within Example 5. Finally, two other formula compositions, one containing 1.75% Hectabrite AW, 3.0% Vee-Gum® T, 5% Van-Gel® O, and 1.75% Cab-o-sil® and the other containing 4.0% Hectabrite AW, 2.5% Vee-Gum® T, and 5.0% Cab-o-sil® were not as stable, but could potentially be used depending on the application.

TABLE 7

Off-gassing for a formula containing 72.5% trichloroisocyanuric acid, 8% aluminum sulfate, 8% sodium tetraborate pentahydrate.

| Formulation | Titrant Volume (ml) |
| --- | --- |
| 72.5% trichloroisocyanuric acid and 1.75% Hectabrite AW, 3.0% Vee-Gum T, 5% Van-Gel-O, and 1.75% Cab-o-sil ® | 3.85 |
| 72.5% trichloroisocyanuric acid and 4.0% Hectabrite AW, 2.5% Vee-Gum T, and 5.0% Cab-o-sil ® | 3.50 |
| 72.5% trichloroisocyanuric acid and 4.0% Hectabrite AW, 3.0% Vee-Gum T, and 4.5% disodium cyanurate | 1.50 |
| 72.5% trichloroisocyanuric acid and 3.0% Vee-Gum T, and 8.5% disodium cyanurate | 1.60 |
| 74.5% trichloroisocyanuric acid and 11.5% disodium cyanurate | 1.00 |

The Example 5 solubility data (Table 8) shows the solubility rates for the Example 5 formula compositions as well as a blend of trichloroisocyanuric acid and sodium carbonate. The results indicate the most stable formula composition from Table 7 (11.5% disodium cyanurate) had a significant dissolution rate increase relative to 100% trichloroisocyanuric acid. This dissolution rate is slightly better than the dissolution rate of the relatively unstable trichloroisocyanuric acid and sodium carbonate blend. Overall, the formula composition containing 1.75% Hectabrite AW, 3.0% Vee-Gum® T, 5% Van-Gel® O, and 1.75% Cab-o-sil® had the highest dissolution rate. Other relatively stable formula compositions such as: 4.0% Hectabrite AW, 2.5% Vee-Gum® T, and 5.0% Cab-o-sil®; 4.0% Hectabrite AW, 3.0% Vee-Gum® T, and 4.5% disodium cyanurate and 3.0% Vee-Gum® T and 8.5% disodium cyanurate had good solubility rates as indicated in Table 8.

TABLE 8

Solubility for a formula containing 72.5% trichloroisocyanuric acid (65% available chlorine), 8% aluminum sulfate, 8% sodium tetraborate pentahydrate.

| Formulation | Titrant Volume (ml) |
| --- | --- |
| 72.5% trichloroisocyanuric acid and 1.75% Hectabrite AW, 3.0% Vee-Gum ® T, 5% Van-Gel ® O, and 1.75% Cab-o-sil ® | 6.28 |
| 72.5% trichloroisocyanuric acid and 4.0% Hectabrite AW, 2.5% Vee-Gum ® T, and 5.0% Cab-o-sil ® | 5.08 |
| 72.5% trichloroisocyanuric acid and 4.0% Hectabrite AW, 3.0% Vee-Gum ® T, and 4.5% disodium cyanurate | 4.22 |
| 72.5% trichloroisocyanuric acid and 3.0% Vee-Gum ® T, and 8.5% disodium cyanurate | 4.67 |
| 72.5% trichloroisocyanuric acid and 11.5% disodium cyanurate | 4.88 |
| 75% trichloroisocyanuric acid and 25% sodium carbonate (Granular Blend) | 4.45 |
| 100% trichloroisocyanuric acid | 0.8 |

EXAMPLE 6

A formula composition containing trichloroisocyanuric acid and disodium cyanurate was prepared. The formula composition was processed as described above.

The Example 6 data (Table 9) shows a formula composition containing 60.0% disodium cyanurate had reasonable stability relative to the 100% trichloroisocyanuric acid control. The solubility data for the 60% disodium cyanurate formula composition was 5.18 ml, remarkably better than the control. Theoretically, an approximate titrant volume of 5.4 ml 0.010N sodium thiosulfate would indicate complete solubilization of all the trichloroisocyanuric acid in the 60% disodium cyanurate formula composition. Based on this theoretical calculation, the experimental data demonstrated nearly complete solubilization of the available chlorine in the experimental formula composition.

TABLE 9

Solubility and Stability of trichloroisocyanuric acid and disodium cyanurate Formula Compositions.

| Formulation | Solubility Titrant Volume (ml) | Off-Gassing Titrant Volume (ml) |
| --- | --- | --- |
| 100.0% trichloroisocyanuric acid | 1.90 | 2.00 |
| 40.0% trichloroisocyanuric acid and 60.0% disodium cyanurate | 5.18 | 3.40 |

EXAMPLE 7

Example 7 shows how the halogen sanitizing composition of Example 5 containing 11.5% disodium cyanurate compares to calcium hypochlorite in an application. This was accomplished by exposing 2, 4 liter beakers with 3500 ml of synthetic pool water containing about 200 ppm calcium hardness and 125 ppm of total alkalinity (pH≈7.5) to environmental UV light by placing samples outside on a sunny day. An amount equivocal to 10 ppm of available halogen was added into each solution. The samples were periodically tested for chlorine and turbidity (NTU). The results are reported in Table 10. Additionally, FIG. 1 graphically illustrates the reported data.

TABLE 10

Calcium Hypochlorite versus 1,3,5-Trichloro-1,3,5-triazine-2,4,6-trione, Disodium 1,3,5-triazine-2,4,6-trione, Aluminum Sulfate, and Borax Formula Composition (Example 5); Test for Halogen Delivery, Halogen Stability, and Water Clarity

| Sampling Time (Hr:Min) | Total Cl: Example 5 Composition | Total Cl: Calcium Hypochlorite | NTU: Example 5 Composition | NTU: Calcium Hypochlorite |
| --- | --- | --- | --- | --- |
| 0:00 | 0.02 | 0.02 | 0.23 | 0.19 |
| 0:05 | 4.1 | 6.8 | | |
| 0:10 | 5.1 | 6.8 | | |
| 0:15 | 9.4 | 7.2 | 0.36 | 1.08 |
| 0:20 | 9.1 | 6.8 | | |
| 0:25 | 8.5 | 6.0 | | |
| 0:30 | 81 | 5.1 | 0.19 | 1.02 |
| 0:40 | 8.1 | 5.0 | 0.25 | 1.43 |
| 0:50 | 6.5 | 3.3 | | |
| 1:00 | 6.3 | 3.5 | 0.17 | 1.35 |
| 1:15 | 6.1 | 2.2 | | |
| 1:30 | 6.1 | 2.6 | 0.19 | 1.32 |

The results in Table 10 and FIG. 1 illustrate the halogen sanitizing composition from Example 5 has superior halogen delivery, superior resistance to UV light degradation, and reduced turbidity relative to calcium hypochlorite.

While the invention has been illustrated and described in detail in the foregoing description, the same is to be considered as illustrative and not restrictive in character, it being understood that only the preferred embodiments have been shown and described, and that all changes and modifications that come within the spirit of the invention are desired to be protected.

We claim:

1. A sanitizing composition, comprising co-compacted granules of:
   (a) between about 40% and about 99% 1,3,5-trichloro-1,3,5-triazine-2,4,6-trione; and
   (b) between about 1% and about 60% of a sodium or potassium salt of 1,3,5-triazine-2,4,6-trione.

2. The sanitizing composition of claim 1 wherein said co-compacted granules comprises between about 60% and about 97% 1,3,5-trichloro-1,3,5-triazine-2,4,6-trione, and between about 3% to about 40% of a sodium or potassium salt of 1,3,5-triazine-2,4,6-trione.

3. The sanitizing composition of claim 1 wherein said sodium or potassium salt of 1,3,5-triazine-2,4,6-trione is disodium cyanurate or dipotassium cyanurate.

4. The sanitizing composition of claim 1 wherein said composition further includes a second disintegration agent, wherein said second disintegration agent differs in composition from 1,3,5-triazine-2,4,6-trione.

5. The sanitizing composition of claim 4 wherein said second disintegration agent is present in an amount of between about 0.1% to about 20%.

6. The sanitizing composition of claim 4 wherein said second disintegration agent is present in an amount of between about 1.0% to about 10%.

7. The sanitizing composition of claim 4 wherein said second disintegration agent comprises an inorganic disintegration agent selected from the group consisting of natural water swellable clays, synthetic water swellable clays, and amorphous silica.

8. The sanitizing composition of claim 4 wherein said second disintegration agent comprises an organic disintegration agent selected from the group consisting of cellulosic compounds, high molecular weight polymers, and the cross-linked forms of said polymers.

9. The sanitizing composition of claim 1, and further including between about 1% to about 40% of an algaestat/algaecide and/or fungicide compound.

10. The sanitizing composition of claim 9 wherein said algaestat/algaecide and/or fungicide is present in an amount of between about 4% to about 18%.

11. The sanitizing composition of claim 10 wherein said algaestat/algaecide and/or fungicide is a boron-releasing compound.

12. The sanitizing composition of claim 11 wherein said boron-releasing compound is selected from boric acid, boric oxide (anhydrous boric acid), compounds having the formula $M_nB_xO_y \cdot ZH_2O$ (in which M is ammonia or any alkali metal or alkaline earth cation, including, but not limited to, sodium, potassium, calcium and magnesium; n is equal to 1, 2 or 3; x is any whole number from 2 to 10; Y is equal to $3X/2+1$; and Z is equal to 0 to 18).

13. The sanitizing composition of claim 12, where the boron releasing compound is sodium tetraborate pentahydrate.

14. The sanitizing composition of claim 1, including between about 1% to about 40% of a water clarifier, coagulant, or flocculant.

15. The sanitizing composition of claim 14 wherein said water clarifier, coagulant, or flocculant is present in an amount of between about 4% to about 18%.

16. The sanitizing composition of claim 14 wherein said water clarifier, coagulant, or flocculant is an aluminum releasing complex.

17. The sanitizing composition of claim 14 wherein said aluminum-releasing complex comprises an aluminum sulfate.

18. The sanitizing composition of claim 1, and additionally including a surfactant.

19. The sanitizing composition of claim 1, and additionally including a glidant.

20. The sanitizing composition of claim 1, and additionally including processing aids.

21. The sanitizing composition of claim 1, and additionally including binders.

22. A method of sanitizing water, said method comprising adding to the water a sanitizingly effective amount of a composition comprising co-compacted granules of:
   (a) between about 40% and about 99% 1,3,5-trichloro-1,3,5-triazine-2,4,6-trione; and
   (b) between about 1% and about 60% of a sodium or potassium salt of 1,3,5-triazine 2,4,6-trione.

* * * * *